(12) United States Patent
Gislason et al.

(10) Patent No.: US 9,474,828 B2
(45) Date of Patent: Oct. 25, 2016

(54) SELF-HARDENING BIOACTIVE CEMENT COMPOSITIONS WITH PARTIALLY DEACETYLATED CHITIN AS BONE GRAFT SUBSTITUTES

(71) Applicant: GENIS hf., Siglufjordur (IS)

(72) Inventors: Johannes Gislason, Mosfellsbaer (IS); Jon M. Einarsson, Reykjavik (IS); Chuen How Ng, Reykjavik (IS)

(73) Assignee: GENIS HF. (IS)

( * ) Notice: Subject to any disclaimer, the term of this patent is extended or adjusted under 35 U.S.C. 154(b) by 0 days.

(21) Appl. No.: 14/396,257

(22) PCT Filed: Apr. 23, 2013

(86) PCT No.: PCT/IS2013/050003
§ 371 (c)(1),
(2) Date: Jan. 22, 2015

(87) PCT Pub. No.: WO2013/160917
PCT Pub. Date: Oct. 31, 2013

(65) Prior Publication Data
US 2015/0217021 A1    Aug. 6, 2015

(30) Foreign Application Priority Data

Apr. 23, 2012 (IS) .......................................... 050032

(51) Int. Cl.
| | | |
|---|---|---|
| *C08L 5/08* | (2006.01) | |
| *A61L 27/12* | (2006.01) | |
| *A61L 27/20* | (2006.01) | |
| *A61L 27/46* | (2006.01) | |
| *A61L 24/00* | (2006.01) | |
| *A61L 24/08* | (2006.01) | |
| *A61L 27/54* | (2006.01) | |

(52) U.S. Cl.
CPC ............. *A61L 27/20* (2013.01); *A61L 24/0084* (2013.01); *A61L 24/08* (2013.01); *A61L 27/12* (2013.01); *A61L 27/46* (2013.01); *A61L 27/54* (2013.01); *C08L 5/08* (2013.01); *A61L 2300/412* (2013.01); *A61L 2400/06* (2013.01); *A61L 2430/02* (2013.01)

(58) Field of Classification Search
CPC ..... A61L 27/12; A61L 27/46; A61L 24/008; A61L 24/08
See application file for complete search history.

(56) References Cited

U.S. PATENT DOCUMENTS 5,618,339 A    4/1997  Ito
2010/0021545 A1    1/2010  Chaput et al.

FOREIGN PATENT DOCUMENTS

| WO | 0141822 A1 | 6/2001 |
|---|---|---|
| WO | 03026677 A1 | 4/2003 |
| WO | 2006057011 A2 | 6/2006 |
| WO | 2006134614 A1 | 12/2006 |
| WO | 2008063791 A2 | 5/2008 |

OTHER PUBLICATIONS

CN101057979A; Oct. 24, 2007; English Abstract Only (1 page).
International Search Report and the Written Opinion of the International Searching Authority, or the Declaration; International Application No. PCT/IS2013/050003; International Filing Date Apr. 23, 2013; 9 pages.
Search Report—Iceland; Case No. 050032; Date of Completion of Search Aug. 31, 2012; 1 page.
Chae Cho et al., "Effect of Calcium Sulfate-Chitosan Composite: Pellet on Bone Formation in Bone Defect", J. Craniofacial Surgery, vol. 16, No. 2 Mar. 2005, pp. 213-224.
Hren et al "Spontaneous bone healing of the large bone defects in the mandible" International Journal of Oral and Maxillofacial Surgery, vol. 37, Issue 12, Dec. 2008, pp. 1111-1116.
João Paulo Mardegan Issa et. al., "Bone repair in rat mandible by rhBMP-2 associated with two carriers", Micron, vol. 39, Issue 4, Jun. 2008, pp. 373-379.
Klokkevolci et al., "Osteogenesis Enhanced by Chitosan (Poly-N-Acetyl Glucosaminoglycan) In Vitro", J Periodontol, Nov. 1996, 67(11), 1170-75.
Oneida A. Arosarena et al. Bone regeneration in the rat mandible with bone morphogenetic protein-2: A comparison of two carriers; Otolaryngology—Head and Neck Surgery, vol. 132, Issue 4, Apr. 2005, pp. 592-597.
Schliephake, et.al., Bone formation in trabecular bone cell seeded scaffolds used for reconstruction of the rat mandible, International Journal of Oral and Maxillofacial Surgery, vol. 38, Issue 2, Feb. 2009, pp. 166-172.
Venkatesan and Kim, "Chitosan Composites for Bone Tissue Engineering—An Overview", Mar Drugs 2010; 8(8), 2252-2266.
Yamada et al., "Mineralization of matrix vesicles isolated from a human osteosarcoma cell line in culture with water-soluble chitosan-containing medium", J. Biomed. Mat Research, vol. 66A, No. 3, Sep. 1, 2003, pp. 500-506.

*Primary Examiner* — Gina Justice
(74) *Attorney, Agent, or Firm* — Cantor Colburn LLP

(57) ABSTRACT

A composition kit for bone healing medical treatment, comprising partially deacetylated chitin (PDC) with a degree of deacetylation in the range of 40-75%. The composition is provided as a kit with a solids fraction and a liquid fraction, provided in separate vials and to be mixed just prior to use. The weight:weight ratio of the solids to liquid fraction is in the range from 1:1.2 to 1:6, and preferably from 1:1.5 to 1:4. The solids fraction comprises the PDC material and calcium phosphate and the liquid fraction comprises water and an acid.

24 Claims, 10 Drawing Sheets

SELF-HARDENING BIOACTIVE CEMENT COMPOSITIONS WITH PARTIALLY DEACETYLATED CHITIN AS BONE GRAFT SUBSTITUTES

FIELD OF INVENTION

The invention is within the field of medical treatment of bone fractures and bone defects, and relates to compounds and compositions of partially deacetylated chitin, and their medical use.

TECHNICAL BACKGROUND AND PRIOR ART

When disease or trauma causes a skeletal void, or whenever healing of a fracture is impaired, a common surgical technique involves harvesting of bone from the iliac crest and transferring the bone graft to the injury site. This is referred to as a bone autograft. The autograft is used to fill the bone void providing osteoconductive and osteogenic properties necessary for effective healing of the injury. This technology is generally regarded as the golden standard in orthopedic surgery but carries severe drawbacks due to frequent morbidity associated with the bone harvest. Hence, bone graft substitutes, possessing osteoconductive and osteogenic properties have been desired by industry and academia alike aiming to eliminate the need for bone autografts. Such bone graft substitutes are generally referred to as synthetic bone graft substitutes. So far, no single product has appeared, proven to provide osteoconductive as well as osteogenic properties to a substantially bone deficient injury side.

Chitin is a natural biopolymer which is obtainable from crustacean shell, but can also be obtained from other invertebrates and from fungi. By deacetylation of the N-acetyl glucosamine residues of the chitin polymer, typically by hydrolyzing the N-acetyl linkages with concentrated alkali, chitosan is obtained. By definition, chitosan is generally described as a copolymer of D-glucosamine (D) and N-acetyl-D-glucosamine (A), which is insoluble in water at pH above 6.2—the isoelectric point of the free amine group—but dissolves at pH below about 6.2. Typically, about 75-100% of the monomeric units in conventional chitosan copolymer are D-glucosamine, which can be described as 75-100% deacetylated chitosan, or as having a degree of deacetylation (DD) of 75-100%. Accordingly, 0-25% of the monomers in such material are N-acetyl-D-glucosamine groups (A).

When the degree of deacetylation is lower than about 75%, the chitin polymer displays different solubility properties, such material, with DD from about 75% down to about 40%, is generally referred to as partially deacetylated chitin, referred to herein as PDC.

The present inventors have previously described biological properties of partially deacetylated chitin polymer and oligomers. WO 03/026677 describes the use of PDC oligomers for treating rheumatoid conditions. WO 2006/134614 discusses biological properties of partially deacetylated chitin polymer and oligomer and discusses how such oligomers act as blockers for chitinase enzymes.

Chae Cho et al. (J. Craniofacial Surgery Vol. 16 No 2 Mar. 2005) describe experiments with solid pellets with chitosan-calcium sulfate composite and their effects on the osteogenesis of defective tibia in rabbits, using chitosan with 90% DD.

Yamada et al. (J. Biomed. Mat Research Vol. 66A no. 3, 1 Sep. 2003, pp 500-506) investigate and discuss effects of chitosan on biologic mineralization and investigated effects of chitosan supplemented into culture medium on osteoblasts.

Klokkevold et al. (J Periodontol. 1996 November; 67(11):1170-75) evaluated the effect of chitosan on the differentiation of osteoprogenitor cells.

WO 2004/028578 discloses a composition for stimulating bone-formation and bone-consolidation that comprises bone morphogenic protein (BMP) as an active ingredient in a formulation with solutions of tripolyphosphate and chitosan, where the two solutions will instantly solidify upon mixing, causing specific handling concerns in the clinic.

WO 01/41822 describes self-gelling mineral-polymer hybrid formulations that comprise (i) a water-based thermogelling liquid component that comprises dissolved chitosan and has a pH between 6.5 and 7.4, and (ii) a solid component comprising calcium, said liquid and solid components are to be mixed together to form a non-hardening thermo-gelling composition, which forms a gel at body temperature.

WO 2006/057011 discloses solid implants of co-precipitated hydroxyapatite and chitosan in 1:1 ratio (chitosan having a degree of deacetylation of 87%), and compositions with "putty"-like consistency, containing a total of 5% chitosan, calcium phosphate and polydimethylsiloxane, and a solid-to-liquid ratio of 2:1. Setting time of the putty-paste was a little less than 6 minutes. The paste was tested for healing induced bone injury in rats.

It is generally held in the art that chitosan itself is not osteoconductive (see e.g. Venkatesan and Kim, "Chitosan Composites for Bone Tissue Engineering—An Overview", Mar Drugs 2010; 8(8): 2252-2266.

Further development of alternative and more effective products, practical for clinical applications is still much appreciated, for effective and low cost bone healing treatments.

SUMMARY OF INVENTION

The present inventors have carefully studied the biological effects of partially deacetylated chitin (PDC) polymers and oligomers and developed new and effective compositions stimulating regeneration of new bone tissue. The invention provides injectable in situ self-hardening bioactive cement material. The compositions of the invention are useful as artificial bone graft substitutes.

The compositions have several practical benefits, such as:
Natural and non-toxic ingredients, no fumes or odours during mixing,
Good biocompatibility and exempt of foreign body reaction by the host tissue,
Low heat generation during curing,
Allows injection and filling of voids without any relevant leakage,
Good mouldability and injectability that allows application with minimally invasive techniques (injection),
Cohesiveness and good wet field properties, allowing injection into humid environment without excessive dissolution or loss of integrity,
Suitable working time, allowing appropriate applying time, with relatively fast curing in situ,
Close to physiological pH and salinity upon curing in situ,
Good bulk capacity, allows admix of liquid constituents like blood or blood components, bone marrow or solution of protein isolates, etc.

Prevents scar tissue formation in the injured host bone tissue and promotes regeneration of new bone tissue on the surface and inside the void filling composition.

Possesses beneficial antimicrobial properties and thus helps to minimize risk of infection.

The new compositions of the present invention rely on properties of PDC that are dependent on the degree of deacetylation and molecular weight, and uses PDC with a degree of deacetylation in the range of 40-75%. Other parameters can be suitably optimized as further described herein.

The present compositions are provided as kits with a solid fraction comprising PDC and a liquid fraction, to be mixed prior to use. The admixed compositions contain a low solid to liquid ratio, in the range of 1:1.2 to 1:6 and more preferably in the range of 1:1.5 to 1:4.

The invention further provides methods for healing bone defects and conditions such as bone fractures.

DETAILED DESCRIPTION

Figure 1:
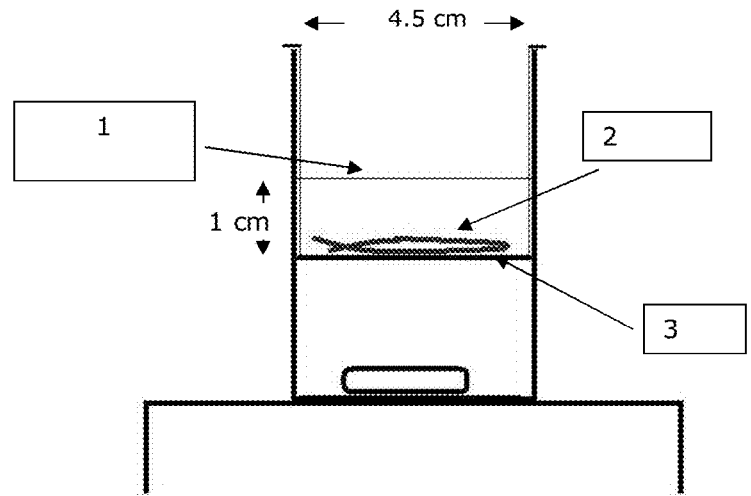
FIG. 1: Illustration of setup for measuring cohesiveness/demixing. (1) water level, (2) cement composition, (3) mesh net.

The present invention provides easy-to-use kits suitable for bone surgery, comprising solid and liquid fractions which are packed separately and sterilized by gamma irradiation. Just prior to operation, the liquid fraction is mixed with the solid fraction to produce liquid or paste-like cement. The cement mix can conveniently be injected into bone voids or fractures and possesses good mouldability and good cohesiveness. It also allows application in bone using minimally invasive techniques such as by injections through a needle. In other embodiments the composition is applied on an existing bone surface e.g. with spatula or the like instrument.

As explained herein, the present compositions are optimized to both provide mechanical support to bone defects and enhance regeneration of new bone tissue by stimulating osteogenic cells to reside and proliferate at the surface and inside the implanted composite material. This is obtained by creating desirable physiological conditions, such as in terms of pH and salinity, and by facilitating cell penetration and biodegradability/resorption of the composite by means of controlling the solid-liquid ratio. The current invention is optimized to control physicochemical and biological properties of the implanted composite. This may involve one or more of the following: controlling the pH through buffering capacity of the acid of the composition (which is preferably phosphoric acid) and partially deacetylated chitin, control of ion strength by careful selection of electrolytes and control of the water binding capacity/wet field properties and injection force by appropriate adjustment of the degree of acetylation of the PDC polymer and relative amount of PDC in the composition. Biological stimulus of osteogenic cells is obtained through in situ hydrolysis of the PDC by endogenous family 18 chitinases, expressed by various cells of the immune system. This is supported by our data shown and discussed further in Example 3 (See Example 3 "Results"). This will generate sustained release of biologically active molecular species of PDC oligosaccharides. Hence, these oligomeric molecules will be gradually released as the composite material degrades, and diffuse into the adjacent tissues providing sustained stimulus to osteogenic cells to invade the degenerating composite which in turn will be replaced by new bone tissue. For optimization of this entire process, the solid-to-liquid ratio plays a key role.

Accordingly, to optimize for the above properties, it has surprisingly been found advantageous that the admixed compositions contain a low solid to liquid fraction ratio, in the range of about 1:1.2 to about 1:6. This corresponds to a range of about 14 wt % to 45 wt % of the solid fraction in the combined mixture. Preferably the compositions have a solid to liquid fraction ratio in the range of about 1:1.3 to about 1:4 or in the range from about 1:1.3 to about 1:3, and more preferably in the range from about 1:1.5 to about 1:3, such as in the range of about 1:2 to about 1:3, including but not limited to ratios of 1:1.2, 1:1.33, 1:1.5, 1:1.8, 1:2, 1:2.25, 1:2.5, 1:3, and 1:4. (These ratios correspond to a weight content of the solid fraction in the combined mixture of 44.4%, 42.9%, 40%, 35.7%, 33.3%, 30.8%, 28.6%, 25%, and 20%.)

The cement compositions with the preferred solid-to-liquid (S/L) ratio have good cohesiveness (show little demixing) in the human body and good wet field properties with minimal dissolution, meaning that the material maintains its integrity and does not spread from the site of injection. This allows good cavity filling capability, including infiltration into spongy and porous bone combined with initial and long term adhesion to bone tissue. While low S/L ratio may result in reduced mechanical strength of cement, the optimized S/L ratio and chitosan content facilitates faster cement degradation, allowing more efficient penetration of cells into the composite and osteogenic PDC and hydroxyapatite to be available for early onset of bone regeneration. Hence, low initial mechanical strength is compensated by early onset of osteogenesis and subsequent buildup of new bone, rapidly taking up the mechanical load.

The mechanical strength can be assessed in a number of ways, some of which are described in the accompanying Example 1. In certain embodiments the compositions of the invention have a mechanical strength measured as ultimate compression strength, after 24 h setting at 37° C. in saline solution (0.9% NaCl), in the range of 0.2 to 10 $N/mm^2$, such as in the range of 0.5-5 $N/mm^2$ or in the range of 0.5-2.5 N.

As a result of the desired low S/L ratio of the compositions, the cured cement composites of the invention will have substantial content of free water, indicating the open, porous nature of the formed composite implant. Accordingly, the compositions of the invention have in preferred embodiments a content of free water after curing (water released by drying at 105° C. for 24 h) in the range of about 40-90%, or more preferably in the range of 40-70 wt %, such as in the range of 50-70 wt %, such as in the range of about 55-65 wt %, and more preferably in the range of about 60-65 wt %, such as about 60 wt %. These values refer to measured free water content in vitro formed cement, cured for 24 h in saline solution (0.9% NaCl). Generally, the lower the S/L ratio, the more water loss during drying of the cured composite. As an example, a S/L ratio of 2 may result in water loss of about 60±5% of the cured wet weight.

Cohesiveness/dissolution or loss of integrity can be assessed in various ways. The inventors have found it useful to assess this property by placing an amount of freshly mixed composition on a mesh net (e.g. approx. 1 mm mesh) below the liquid surface in a beaker with saline solution, where the solution is stirred with a magnetic bar. (See further description in Example 1.) Preferably, after a brief period of stirring such as for 10 min, substantially all of the material is still adhering, such as more than 95%, or more preferably more than 98% and yet more preferably more than 99% and most preferably more than 99.9%.

The mixed composition cement preferably has a pH close to neutral, or in the range of about 6.0 to 7.8 and more preferably in the range of 6.5 to 7.4, most preferably about pH 7. The solid fraction containing calcium phosphate will generally be substantially alkaline, while the liquid fraction typically is acidic in order to neutralize the alkaline phosphates. In preferred embodiments, the liquid fraction comprises one or more acid selected from but not limited to phosphoric acid, hydrochloric acid, ascorbic acid, lactic acid, acetic acid, citric acid, formic acid, propionic acid, malic acid, and glutamic acid. The suitable concentration/amount of acid sufficient to neutralize the mixed composition depends on the S/L ratio of the composition, on the amount of phosphates as well as the DD of the PDC. With lower S/L ratio (less solids) less amount of acid is needed. The preferred acid in present embodiments is phosphoric acid. In preferred embodiments the liquid component comprises at least about 5% phosphoric acid, such as in the range of about 2.5-20 wt % phosphoric acid, such as in the range of 2.5-15 wt % or in the range 5-15%, such as about 5%, about 8%, about 10%, about 12% or about 15%. In other useful embodiments, the liquid fraction comprises one or more other acid, as an alternative or in addition to phosphoric acid, such as any one or more of the above mentioned acids. In these embodiments, the total amount of acid should preferably be sufficient to substantially neutralize the solution after mixing the alkaline solid fraction with the liquid fraction. Accordingly, it is preferred that the acidity be at least the same as for a 5% phosphoric acid solution. Accordingly, the liquid fraction may suitably have a pH in the range of about 1 to 2.5, and more preferably in the range of about 1 to 2. In other embodiments, the acidity can be attained by providing an amount of acid in the liquid fraction that has equivalent normality (N) to a 5% phosphoric acid solution, or higher acid strength, such as mentioned above.

The PDC itself also has buffering capacity, thus conventional calcium phosphate self-hardening composites show a faster and less controllable pH drop during curing compared to preferred compositions of the current invention. The presence of PDC means that the PDC can consume (neutralize) residual protons during formation of hydroxyapatite, and thereby reduce pH change.

It follows that if other acids are used in addition to or instead of phosphoric acid, more calcium phosphate may be needed to provide sufficient phosphate content. In the overall composition, after mixing the solid and liquid fraction, the acid content of the thus obtained composition is preferably at least about 2.0% phosphoric acid, or an equivalent of other acid(s) with or without phosphoric acid, such as in the range of about 2.5-25%, such as about 3.5-15%, or in range 5-10% phosphoric acid or equivalence thereof.

The compositions of the present invention have good injectability. The optimal injection force to inject 2-3 mL fresh cement composition of the invention, with a 5 mL syringe (B.Braun or equivalent) with 12 mm ID and 2 mm outlet, is preferably in the range of about 10-30 N, and more preferably not higher than about 20 N, and more preferably less than about 15 N or less than about 10 N. This can be measured as described in Example 1.

The compositions of the invention comprise PDC incorporated in the solid fraction; this has a decisive role in setting of the cement. The higher the degree of deacetylation (DD), the shorter is the setting time. On the other hand, the setting is temperature-linked, i.e. the higher the temperature the faster is the setting time. Thus cement setting time may be regulated by selecting PDC with suitable parameters and thereby optimizing the composition according to actual operation needs. At room temperature (20-25° C.) with 50% DD PDC, the setting time attained is 30 min, while at <5° C., the setting time may extend to >3 h.

The term setting time as used herein refers to the timepoint from mixing when the cement has hardened to such extent that it cannot be readily applied as described herein and can no longer be moulded without breaking.

Another useful term is working time or using time, which refers to the time within which the composition can be worked/used, after initial mixing (and brief waiting for the composition to become sufficiently coherent) and until setting time is reached. For the compositions of the present invention, the using time at room temperature (20-25° C.) is preferably between 2-25 minutes from initial mixing, such 2-20 minutes or 3-20 minutes from mixing. This may vary depending on the exact composition and temperature in the operation room. Generally, for lower S/L ratio composition, the period of waiting for onset of working time is longer, such as in the range of 3-8 minutes for S/L ratio in the range of 1:2 to 1:3, but this is compensated with a later setting time. Accordingly, when the S/L ratio is 1:1.5 the working time at room temperature is generally from about 2 minutes from mixing to about 9 minutes, whereas when the S/L ratio is lower, such as 1:2, the working time is from about 6 minutes from mixing, lasting until about 20 minutes from mixing, thus giving longer using time. With even lower S/L values (such as 1:2.5 or 1:3) the working time is further shifted, starting even later after mixing but the composition remains workable for a longer time.

Desired mechanical strength is typically attained by adjusting the relative amount of PDC, which is crucial for the mechanical properties of the cement. The cement reaches peak compression strength at about 20% PDC, w/w, of total cement. Generally, it is possible to prepare cement with 50% PDC, w/w. The compositions of the present invention comprise in preferred embodiments an amount of PDC being 10 wt % or less of total weight of the combined composition (solid and liquid fractions), such as in the range of about 2-10% of the combined fractions, and in some embodiments in the range of about 2.5-5%.

Furthermore, the amount of PDC in the cement compositions has an effect on osteogenic effect when applied into a bone void or to a bone fracture, higher amount producing more osteogenic effect.

For the compositions of the invention, the solids fraction preferably comprises in the range of 3-30 wt % PDC; cement with more than the said amount of PDC may induce excessive bone growth, depending on the degree and pattern of acetylation. More preferably the solids fraction comprises PDC in the range of 5-15 wt %, such as in the range of 5-10%.

It is preferred that the PDC in the inventive compositions comprise regenerated polymer, which has undergone a dissolution and subsequent filtering of impurities and to remove endotoxins from the matrix and thereafter dried in a suitable drying process. This regenerated chitosan may in other embodiments be replaced by classical chitosan or partially deacetylated chitin with similar degree of deacetylation, molecular weight and particle size, provided it is substantially pure and contains low levels of endotoxins. Furthermore, salt form or other form of chemically modified PDC or chitosan, such as quaternary chitosan, carboxymethyl chitosan, etc., may be used for the formulation of cement in certain embodiments of the invention.

The PDC in the compositions of the invention is preferably highly purified PDC with endotoxins levels less than 100 EU/g. This secures good biocompatibility of the cement and provides instant osteogenic effects when in contact with bone tissue.

As mentioned, the PDC material used in the invention has a degree of deacetylation in the range of 40-75%, and more preferably in the range of about 40-70%, such as in the range of about 40-60%, including about 40%, about 45%, about 50%, or in the range of about 50-60%, such as e.g. 55% or 60% DD.

Furthermore, the PDC is preferably deacetylated to randomized form during deacetylation process (i.e. deacetylation of chitin, which is the preferred way of obtaining suitable chitin derivative for the present invention), such that presence of blockwise N-acetyl-D-glucosamine (A) or D-glucosamine (D) moieties, e.g. A-A-A-A or D-D-D-D, is minimized. Upon hydrolysis by endogenous chitinases in the body, such desired semi-randomly deacetylated material produces optimal length of oligomers, in terms of its amount, molecular weight, blocking of family 18 chitinases and affinity to chitinase-like proteins, to obtain optimal therapeutic purposes for bone tissue regeneration.

The degree of deacetylation and distribution of remaining acetyl groups has a marked influence on osteogenic activities of the PDC polymers and oligomers. The lower the deacetylation and the more homogenous distribution of acetyl groups, the more osteogenic activity is displayed by the PDC. In a preferred embodiment of the invention, a semi-homogenous distribution is favored, i.e. not a block distribution as mentioned above and not a fully homogeneous even distribution of the acetyl groups meaning (as an example, in PDC with 50% DD, N-acetyl glucosamine residues must not be 100% distributed as every other monomer).

The molecular weight (MW) of the PDC as referred to herein refers to weight average molecular weight of the PDC polymer. The MW of PDC affects various properties of the compositions; these include mechanical strength, injectability, mouldability, cohesiveness or demixing, filling capacity, setting time, etc. The preferred workable MW is in range of 10-1000 kDa, accordingly, the preferred MW of the PDC in the compositions of the invention is within said range. Mouldability and demixing properties are improved as the MW increases; however, very high MW may not act favorably on injectability and filling capacity. For the compositions of the invention, the preferred range of the chitin material is within 30-200 kDa.

A mixture of high and low MW may compromise various conflicting properties, e.g. injectability vs. demixing properties. On the other hand, the incorporation of therapeutic PDC in oligomer form may shorten the healing process. In certain embodiments the compositions comprise partially deacetylated chitooligomers, typically with oligomer length in the range of about 3-12 sugar residues in the oligomer chain, and a DD value in the range of about 30-70%, as part of the PDC material, such as about 5-25 wt % of the total content of the PDC material, such as about 5%, 10% or 15%. This will promote an early onset of osteogenesis.

After the kit has been prepared and packaged, sterilization with gamma irradiation is preferred. The gamma irradiation may affect the MW of the initial PDC material, thus if the initial PDC material in the compositions prior to irradiation have a MW ranging between 200 and 1000 kDa, the irradiation may render final MW of 30-200 kDa after gamma irradiation. The effective initial MW may in some embodiments range from 10 to more than 1500 kDa, and the final MW may range from 10 to 1000 kDa. The most preferred range for final MW is as mentioned above within a range of 30-200 kDa and accordingly a preferred initial MW range is within 20-1000 kDa, such as in the range 100-1000 kDa, and more preferably in the range 200-1000 kDa, as measured by GPC/SEC system using light scattering detector.

The workable dose of gamma irradiation in the context herein is preferably in the range from 9 to 100 kGray, the optimum preferred dosage is in the range of 20-35 kGray.

Preferably, the PDC in the compositions of the invention has a particle size of not more than 500 μm. In an acidic environment, such material dissolves quickly and reacts with calcium phosphates to regulate the cement properties.

As mentioned, the present invention has the PDC incorporated in the solid fraction. This has the added advantage that possible acid degradation during storage is avoided. This secures reasonable shelf-life of the cement and avoids development of both inferior cement properties and economical losses.

Also the calcium phosphates are comprised in the solids fraction of the composition. In the preferred compositions of the invention, the calcium phosphate will form low crystalline precipitated hydroxylapatite, to ensure optimal assimilation and to form bone tissue in the body.

Preferably, the composition solid fraction comprises an acidic calcium phosphate and a basic phosphate. Upon mixing with the liquid fraction and neutralization, the calcium phosphates lead to formation of precipitated hydroxylapatite. The most favorable ratio of calcium to phosphate, Ca/P ratio, is in the range of about 1.6 to 1.7, however, the ratio of Ca/P may be workable in range 1.2 to 2.2, which is the preferred range according to the invention.

Accordingly, in one embodiment, the calcium phosphates are alfa-tricalcium phosphate and tetracalcium phosphate. These preferably have a purity of higher than 80%. (According to inventors' experience, purity of less than 80% can be used as well and may not produce inferior osteogenic properties.) Other combinations of calcium phosphates leading to formation of hydroxylapatite may be used also in this invention.

Calcium sulphate is brittle and provides less strength than calcium phosphates, thus tends to have faster resorption rate than calcium phosphate in the body. A mixture of calcium sulphate and calcium phosphate may combined benefit both the resorption rate and the mechanical properties of the cement in the body.

The calcium phosphate(s) should preferably have a particle size of not more than 180 gn, more preferably less than about 100 μm. The mechanical strength is inversely proportional to the particle size. The most favorable size is 50 μm or less.

In some embodiments, the composition comprises sodium glycerophosphate in the solid fraction. Sodium glycerophosphate may be used to improve further the mechanical properties of the cement and to adjust the salinity of the cement to physiological conditions.

In other embodiments, other phosphates may as well be used, as an alternative or in addition to sodium glycerol phosphate, including sodium hydrogen phosphate, disodium hydrogen phosphate, etc.

As mentioned above, the invention further provides methods that are based on using the compositions of the invention, for healing a fractured bone. The methods comprise providing a solids fraction and a liquid fraction as described above, and in mixing the two fractions together in a ratio in the range from about 1:1.2 solids fraction to liquid fraction to about 1:6, and more preferably in the ranges as described and defined herein above, such as most preferred in the ratio of about 1:2. The two fractions are mixed and the mix allowed to cure for a suitable time until a desired consistency and viscosity is obtained, at this time the "working time" of the composition starts, then the mixture is inserted, preferably by injection to the site of bone fracture which it is desired to heal. The handling of the compositions fits well into clinical procedures involving orthopedic surgery. The product can be used to replace bone grafts when filling bone voids, to promote union in bone fracture healing, to promote fusion such as in spinal fusion operations, ostectomy, e.g. in periodontal surgery, bone cancer surgery such as limb sparing surgical operations, reconstruction of non-unions of peripheral bones, in repair of ostelytic processes in benign processes, etc.

It follows that the invention also provides PDC material as herein described for use as a medicament for repairing and healing bone in general, in particular when the PDC is provided in a composition kit as herein described.

EXAMPLES

Example 1

Material Properties of a Particular Composition of the Invention with S/L Ratio 1:2

The solid and liquid components are mixed separately and combined and mixed with spatula immediately before use.

TABLE 1

| Composition | |
|---|---|
| Component | Relative amount |
| Solids fraction: | |
| Tetracalcium phosphate | 46 |
| alfa-tricalcium phosphate | 35 |
| Sodium glycerol phosphate | 11 |
| PDC, 50% DD | 8 |
| Liquid fraction | |
| Phosphoric acid | 20 |
| Calcium phosphate | 4 |
| water | 176 |

Texture: The cement composition right after mixing has the texture of a milky paste at the beginning of the working time. The injection strength is measured with a 5 mL B.Braun syringe (12 mm ID and 2 mm outlet) in the range 15-30 N.

Working time of the composition at room temperature (20-25° C.) is within 3-25 minutes from initial mixing, i.e. setting time of 25 minutes at room temperature, but up to 3 h at 3° C.

When 2 g of the composition were placed in 5 ml of unbuffered saline water (0.9% NaCl), the initial pH was 7.4. After 6 hours pH was 6.84, after 1 day 6.47, and after 5 days 5.94.

The cohesiveness of the composition was measured as follows:

50 ml of saline water (0.9% NaCl) is placed in 100 mL beaker with a 2.5 cm magnetic stirrer in the bottom and 25 mesh net positioned at depth 1 cm below surface. 0.5 ml ready-to-use cement is injected onto the mesh (in a circular motion to provide a "curly ring" shape). The setup is illustrated in FIG. 1. The solution is stirred for 10 min at speed of 100 rpm. The exact weight of the injected cement is determined (by weighing the weight of syringe before and after injection). After the stirring period the solution is transferred to a turbidity measuring tube and turbidity measured and expressed as NTU).

Calibration curve: Stock suspension was prepared by using respective cement as standard. A weighed portion of cement (accurate to 0.0000 g) is dispersed thoroughly to produce a turbidity of 1000 NTU. The stock suspension was used to prepare standard suspensions with 0, 200, 400, 600, 800 and 1000 NTU through serial dilution. A linear graph was prepared with the amount of cement plotted against the turbidity of the suspension. Thus by measuring turbidity of the test solutions after the 10 min. stirring the amount of dispersed cement was determined.

With this measurement it was determined that <0.1% of the cement composition had been demixed and dispersed in the saline solution.

Further Mechanical Properties:

Resistance to penetration was measured with a load cell by pressing a needle (3 mm OD) to the depth of 5 mm into fully cured composition embedded in 96 well plate, ϕ6.7×13 mm. The composition was cured by incubation in saline solution (0.9% NaCl) at 37° C. for 24 hours. The resistance of the composition listed in Table 1 (S/L ratio 1:2) was measured to be 8.08±0.34 N/mm$^2$ using MTS tester (MTS Insight 10, Eden Prairie, Minn., USA) using 6-8 replicates for each composition.

Penetration was also tested for compositions with varying S/L ratio. A composition with S/L ratio of 1:1.5 has a penetration resistance of 17.25 N/mm$^2$, which is almost threefold as compared to the S/L 1:2 composition, (6,221 N/mm$^2$), whereas a composition with a S/L ratio of 1:1 has a measured penetration resistance of 32.82 N/mm$^2$.

The strength of the cement is calculated from the penetration force at 5 mm displacement. Earlier experiments have shown a linear correlation between penetration tests as described and classical compression test (CCT).

Example 2

Effect of Deacetylation on Mechanical Properties

Figure 2:
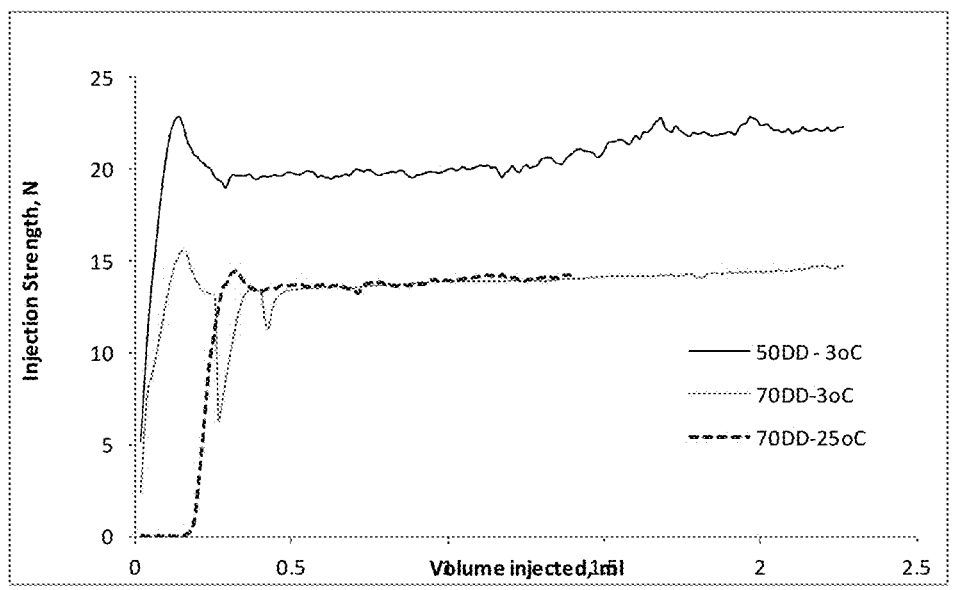
FIG. 2: Measurement of injection strength/resistance of compositions with different degree of deacetylation (DD), see Example 2.

Injection force: Two compositions were formulated as described in Example 1, but with PDC of two different DD values, 50% and 70%. The injection test was conducted in a B. Braun 5 ml syringe with 12 mm ID and 2 mm outlet using MTS tester. Results are shown in FIG. 1. (Tests conducted at either 25° C. or 3° C., see FIG. 2.)

Figure 3:
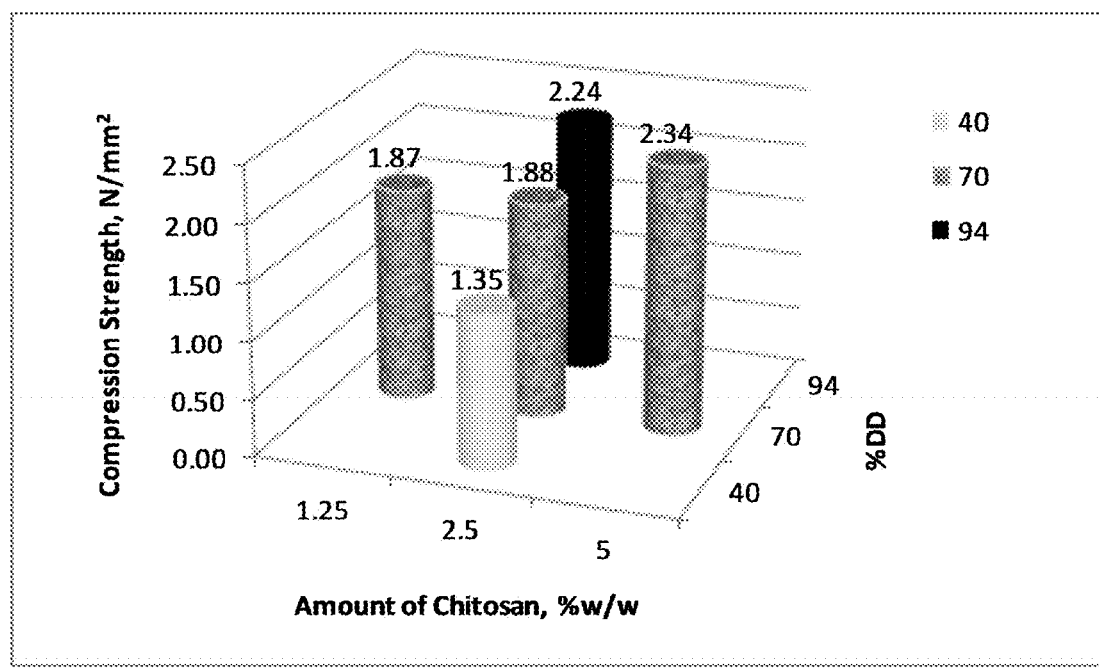
FIG. 3: Compression strength of cement compositions of the invention, with different degree of deacetylation and different amount of PDC.

Compressive strength: Three compositions were prepared as in Example 1, but with PDC of three different DD values, 40%, 70% and 94% and S/L ratio of 1. The compressive strength was tested with 500 N load cell with cross-head speed of 20 mm/min using MTS tester. Initial cement temperature was set at 3 and 25° C. during the test. Results are shown in FIG. 3. There are 5 replicates for each treatment in the compression test, each with size of ϕ9.6×15 mm. These specimens were incubated for curing in saline water (0.9% NaCl) at 37° C. for 24 h and the test condition were as described for the injection test.

Example 3

In Vivo Testing of Compositions in Rat Mandible Model

Optimization of Degree of Deacetylation

Introduction:

The rat mandible (jaw bone) is a frequently used model for bone healing studies (Bone repair in rat mandible by rhBMP-2 associated with two carriers; Micron, Volume 39, Issue 4, June 2008, Pages 373-379, João Paulo Mardegan Issa et. al.; Bone formation in trabecular bone cell seeded scaffolds used for reconstruction of the rat mandible; International Journal of Oral and Maxillofacial Surgery, Volume 38, Issue 2, February 2009, Pages 166-172, H. Schliephake, et. al., Bone regeneration in the rat mandible with bone morphogenetic protein-2: A comparison of two carriers; Otolaryngology—Head and Neck Surgery, Volume 132, Issue 4, April 2005, Pages 592-597, Oneida A. Arosarena, Wesley L. Collins; Spontaneous bone healing of the large bone defects in the mandible; International Journal of Oral and Maxillofacial Surgery, Volume 37, Issue 12, December 2008, Pages 1111-1116, N. Ihan Hren, M. Miljavec).

Figure 4:
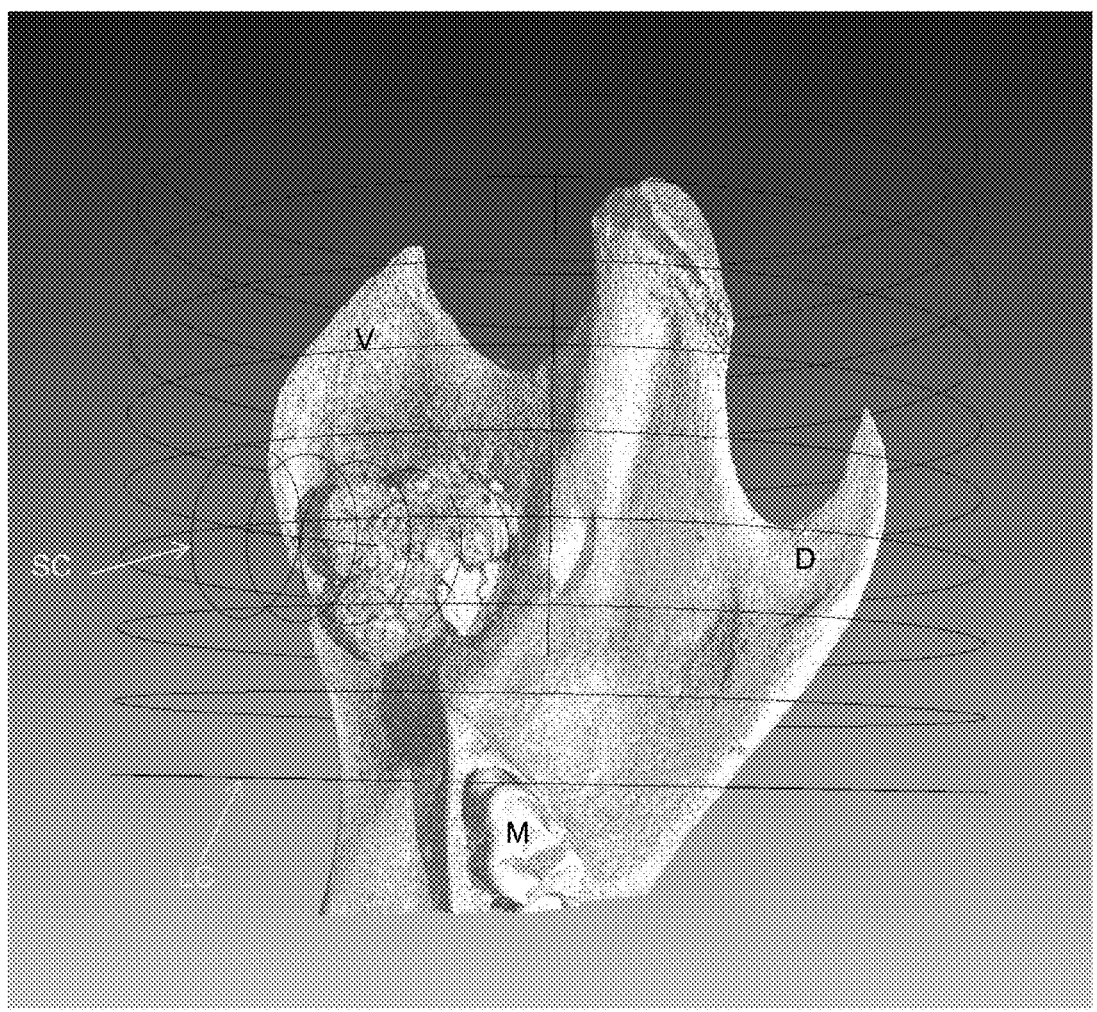
FIG. 4: Standardisation of mandibular volume for micro-CT analysis (see Example 3). Orientation of the larger cylinder (LC) embracing the entire posterior part of the mandible and the small cylinder (SC) embracing the implanted composition.

The mandible is a metabolically active bone responsive to the constant stress caused by feeding and gnawing. We have developed an animal model for critical bone lesion in the rat mandible using micro-CT analysis to measure new bone growth and osteogenic response and histological examination in order to translate mineralized features of the micro-CT constructs into mineralized bone tissue. A drill hole of 4 mm in diameter into the middle area of the masseteric fossa of the rat jaw provides a critical sized void affecting the mechanical properties of the bone (FIG. 4). This ensures that the bone is responsive to the injury, compensating for the weakening of the bone structure by activating appropriate osteogenic responses. The micro-CT analysis enabled quantification of mineralization using a defined part of the mandible (FIG. 4). This proved to be an excellent tool to evaluate osteogenic effect of biomaterials injected to this void as a bone implant. In this study, the model is used to evaluate the bone growth-stimulating effect of different derivatives of chitin in calcium phosphate-based injectible bone void filler. These chitin derivatives were three differently deacetylated chitin polymers, 50%, 70% and 96% deacetylated and one 50% deacetylated oligomer (T-ChOS™, Genis hf., Iceland). Based on our previous rat jaw studies the implant time was adjusted to 7 days. The acetylation of the polymer appeared to be of importance for inducing new bone formation showing the 50 DD polymer to be the most active and the 96% DD polymer to be inactive.

Materials and Methods

The chitin derivatives used in this study were as follows:
50 DD PDC. Degree of deacetylation 50%. (Same material as described in Table 1).
70 DD PDC. Degree of deacetylation 70%.
96 DD chitosan. Degree of deacetylation 96%.
50 DD oligomer (T-ChOS™, Genis hf, Iceland). T-ChOS™ is void of monomers and contains less than 10% dimer and trimer. Octamer is the most abundant oligomer in the composition.

Average molecular weight of all polymers was larger than 130 kDa as judged by size exclusion chromatography.

Kits of the four different implant composites were produced, each kit containing a solid component (solids fraction) and a liquid component (liquid fraction). The solid component (one tube) contained 0.155 g of chitin-derivative, 0.904 g tetracalcium phosphate and 0.701 g alfa-tricalcium phosphate, 0.220 g sodium glycerophosphate and 0.098 g calcium hydroxide (total weight of solids fraction 2.078 g). The liquid component (one tube) contained 0.398 g phosphoric acid and 3.504 g water, total weight of 3.902 g (S/L ratio of 1:1.88).

One solid and one liquid component were put into an aluminum laminated and thermally sealed plastic pouch, producing a complete ready to use kit. All kits were sterilized by gamma irradiation (20 KGy; Radiation Center, Oregon State University, USA).

During operation and prior to implantation, the components were mixed in an aseptic manner, put in a syringe and kept at 4° C. until implantation.

Test animals were Sprague Dawley male rats (260-280 g), supplied by Taconic in Denmark. Animals were inspected clinically at arrival and left to acclimatize and grow in the experimental facility for 30 days prior to operation. At the day of operation, average weight of the animals was 413 g, ranging from 430-464 g. The experiment was conducted under a license from the Icelandic Committee on Animal Experiments Approval (License No. 0709-0405). Operations were performed by orthopedic surgeon and anesthetist, medication dosages and animal welfare was supervised by veterinarian.

Left jaw of each animal was prepared for surgery by shaving and disinfecting. The mandible was accessed through an incision parallel to, and over the inferior border of the mandible. Fossa masseterica was accessed by blunt and atraumatic dissection of the fibers of musculus masseter. A 4 mm hole was drilled through the central part of fossa masseterica, using a 4 mm dental drill. After thorough flushing with sterile saline water (5 ml), the hole was injected with 25 μl of the experimental test formulation using an Eppendorf dispenser or left untreated (empty void control). Surgical wounds were closed with sutures.

A total of 6 groups were established using 39 animals. Table 2 shows the experimental setup.

TABLE 2

Experimental set-up. Number of animals in each group, treatment of the hole and duration of live phase.

| No. of animals | Treatment | Implantation time (days) |
|---|---|---|
| 4 | Empty void | 7 |
| 4 | 70% DD polymer | 0 |
| 8 | 96% DD polymer | 7 |
| 7 | 70% DD polymer | 7 |
| 8 | 50% DD polymer; | 7 |
| 8 | 50% DD oligomers; | 7 |

At termination rats were anaesthetized with Isofluran and under anesthesia terminally bled from the heart. The left jaw was then dissected free from the mandibular joint and placed in 3.7% formaldehyde in 50 mM phosphate buffer, pH 7.0.

Scanning was performed in a micro-CT scanner (Nanotom from General Electric Inspection Technologies). Samples were fixed in a closed plastic cylinder filled with the fixative solution and mounted on the rotational table in the CT-scanner. Scans were performed with an Al-phantom and a plastic phantom (PET) as reference points for gray value comparison. Magnification was 4, voxel size 12.50 μm/voxel edge, number of images collected 1080 (step size 0.33°, with exposure time of 2000 ms, frame averaging of 3, and 1 frame skipped. X-ray settings were 100 kV, 125 pA, using tube mode 0 and no filter.

Volume reconstruction was performed using the Datos-x software accompanying the CT-scanner. Data analysis was performed using Volume Graphics Studio Max 2.0 from Volume Graphics.

A cylindrical volume was defined, comprising the entire bone extending back from the distal edge of the hindmost molar, including the mandibular process, angular process, coronoid process and the hole with or without an implant (FIG. 3; LC). Through gray value cut off/gray value definition, the total bone volume (old and new bone) and implant material within this volume was determined. In case of jaws with an implant, a smaller cylinder was defined perpendicular to the larger cylinder, including the implant material (FIG. 3; SC). Volume of implant material within this cylinder was subtracted from the total bone and implant volume determined by the large cylinder. In this way, an estimate of the total bone volume (new and old bone) of treated and untreated jaws were obtained (FIG. 3).

After micro-CT scanning samples were placed in the buffered fixation solution. Selected samples were decalcified for 3 hrs in Decalc (Histolab, No. 00601, Gothenburg, Sweden). Then the specimens were dehydrated, paraffin embedded, sectioned (2 μm) and stained with Hematoxylin-Eosin. Sections were examined using a light microscope (Leica DM 2000, Germany) connected to a digital camera (Leica DFC 290) and photographed.

Results

Figure 5:
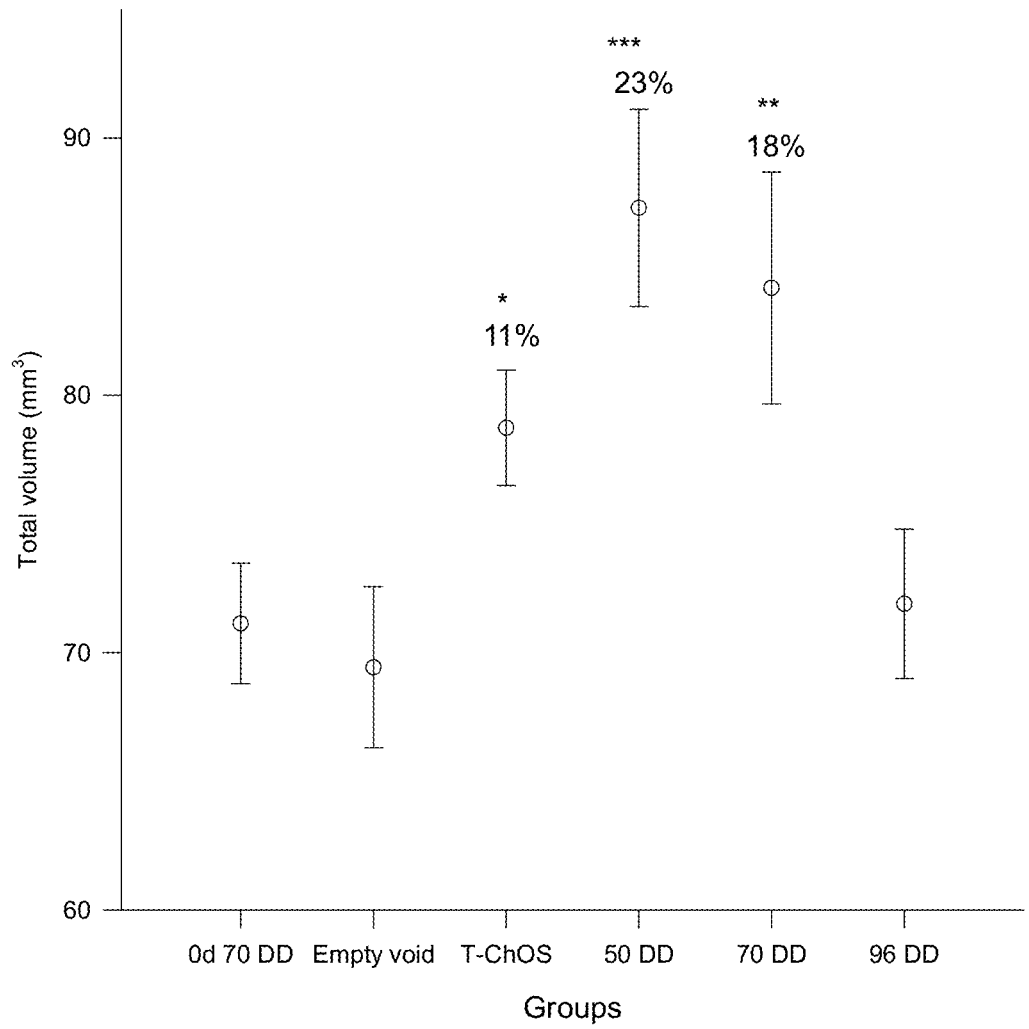
FIG. 5: Total volume formed along the surface of the rat mandible 7 days after implantation compared to total volume at day 0 (0d 70 DD). Mean and SEM of 7-8 individuals (Example 3).

Within the 7 day period there was an acetylated chitosan induced increase in the mineralized jaw bone volume (FIG. 4). Average mineralized bone volume (AMBV, in mm$^3$) was calculated for each group (Mean±SEM). No significant difference was observed between the two control groups (empty void group and zero day group, 69.4±3.1 and 71.1±2.3 respectively; FIG. 5). The AMBV was negatively correlated with the % DD value for the deacetylated chitin polymer; 96DD group had a mean value of 71.9±2.9, the 70DD group a value of 84.2±4.5 and the 50DD group was 87.3±3.8 (FIG. 5). Compared to the empty void group, AMBV in the 70DD and the 50DD groups were significantly increased (18 and 23% respectively). Interestingly the 96DD group (96% deacetylated chitosan) has no significant effect on the mineralized bone volume (FIG. 5).

The oligomer composite (T-ChOS™ implant) induced bone volume by 11% (FIG. 5). This induction was significant (p<0.05). However due to inferior physiochemical properties, the T-ChOS™ implant was often crunched and had relinquished the hole. This was evident when micro-CT scans were examined. Large portions of the T-ChOS™ implants were missing in the drilled holes. The polymer is apparently essential for mechanical stability of this bone cement formulation.

Figure 6:
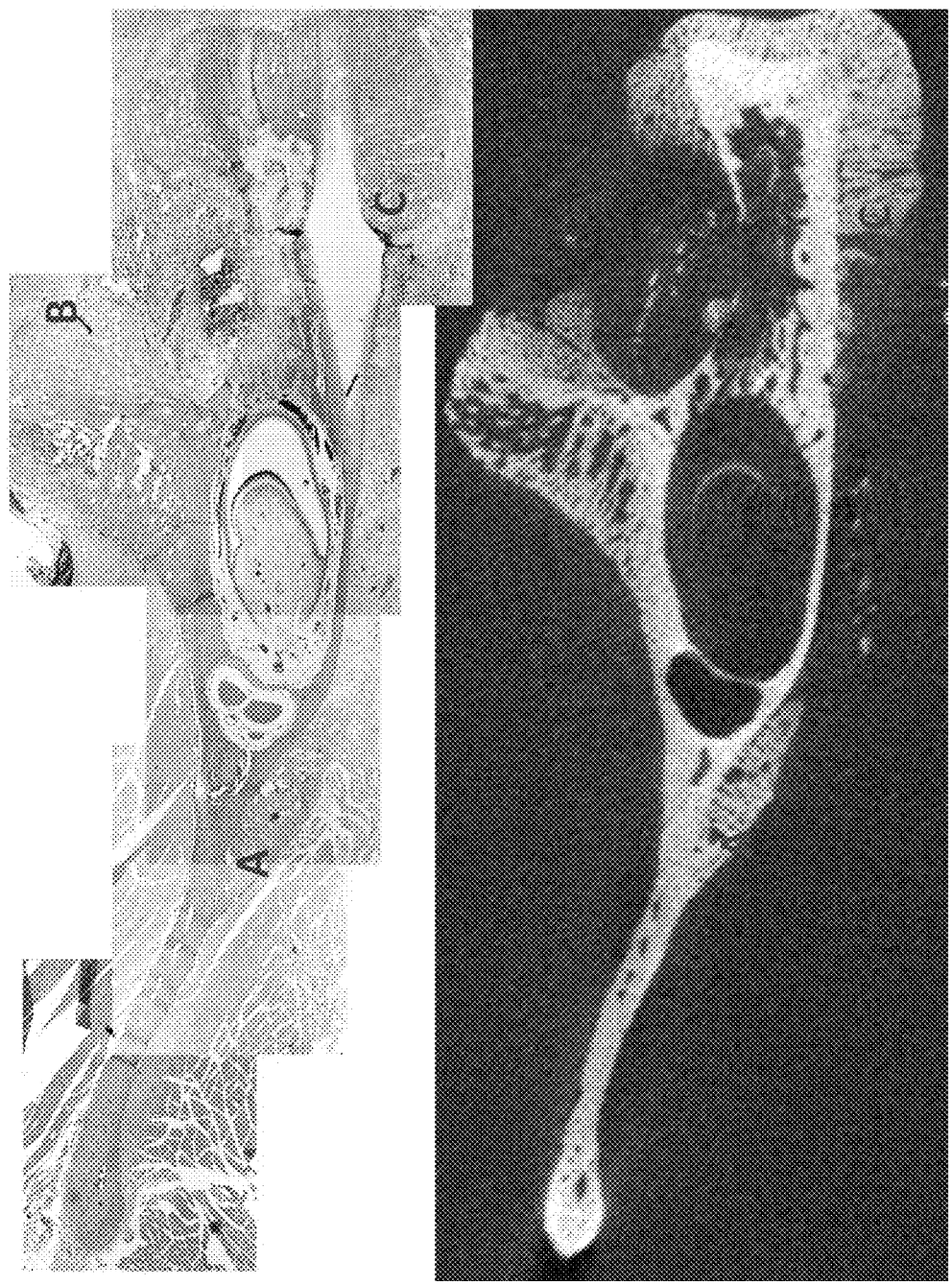
FIG. 6: Transverse section through the mandible of a rat implanted with 70% DD polymer composite, 14 days post-operatively. The section is 1-2 mm frontal to the drilled hole. The upper figure shows a H&E stained paraffin section of the mandible. Lower figure presents a transverse section of a micro-CT construct through the same region of the same mandible (see Example 3).

FIG. 6 shows the comparison of histological and micro-CT transverse sectioning through the same rat mandible 14 days after implanting of 70% DD polymer based injectable composition. The section is 1-2 mm frontal of the drilled hole. Mineralized tissue (A, B and C), characterized as new bone by the micro-CT analysis, appeared to be newly formed bone tissue as judged by the hemotoxilin-eosin stained sections.

All new bone had less density than original jaw bone, judged by micro-CT and histological examination. The histological preparations revealed trabecular bone formation with vascularization within new bone outgrowth. The new bone outgrowth was always from the periosteum covering the outer surface of the bone and not the bone defect itself (FIG. 6). Therefore it can be stated that this PDC induced bone outgrowth was localized distally from the drilled hole throughout the mandibular bone surface, mainly along sites exposed to maximum of mechanical stress within the jaw. This can only be explained by activity of small molecules capable of diffusing throughout the bone related tissues. These small molecules are most likely PDC oligomers formed by in situ hydrolysis of the PDC polymer in the implant. This hydrolysis is most likely catalyzed by family 18 chitinases expressed by white blood cells (neutrophils and macrophages). These active chitinases will cleave the partially acetylated chitin polymers to form various sizes of PDC oligomers. These said PDC oligomers diffuse from the implanted composition into the adjacent tissues and mediate this distal bone growth promotion in response to mechanical stress to the bone.

Example 4

Treatment of Critical Bone Void in Proximal Sheep Tibia

A composition as described in Example 1 (Table 1) and Example 2 was tested by implantation into epiphysis of the proximal tibia of forty-five 5 year old sheep (age 5.83±0.71, Mean±SD). All sheep were operated in a similar manner, 15 were kept for 3 months for a short-term evaluation and 15 were kept for 13 months for long-term evaluation. The experiment was conducted under a license from the Icelandic Committee on Animal Experiments Approval (License No. 0709-0405). Operations were performed by orthopedic surgeon and anesthetist, medication dosages and animal welfare was overseen by veterinarian.

Mixing of the Liquid and Solid Components

The partially deacetylated chitin polymer used in this sample possessed the following properties: 50% degree of deacetylation; 100% solubility in 1% solution of 1% acetic acid; viscosity of solution 460 cP; turbidity in solution <10 NTU; apparent average molecular weight of 330 kDa; endotoxin content 93 EU/g.

The solid and the liquid components of the kit were poured into a sterile plastic cup and stirred and knead together with a sterile spatula for 2 minutes forming a viscous slurry.

Surgical Procedures

A hole of 8 mm in diameter was drilled in the middle between the anterior and posterior borders of the bone and in the height of the tuberositas of the left and right tibia of each animal. The entrance hole was drilled at a right angle through the cortex and thereafter the drill was redirected into a 45° upwards direction ending beneath the floor of the tibia plateau. The drill was not cooled during the drilling procedure. After drilling, the drill hole was thoroughly rinsed of bone debris by flushing with 40-50 ml of sterile saline water and a thorough suction. After mixing the liquid and solid components of the test kit, 1.5 ml of the slurry was put into a 5 ml sterile syringe mounted with a sterile pipette tip and the entire content injected into the drill hole, ensuring that the material reached to fill the entire space of the drill hole from the tibia plateau, down and out to the opening in the cortex. The left leg holes were left empty and used as negative controls. Thereafter the surgical wound in both legs was closed with 4-0 running Vicryl subcutaneous sutures and the skin with 4-0 Etilone continuous intracutaneous suture. After surgery and wake-up, the animals were moved back to the sheep pen for recovery where they were carefully monitored until ambulatory.

Post Mortem Treatment of Samples

Bone samples were put into 3.7% formaldehyde in 50 mM phosphate buffer, pH 7.0 immediately after explantation and thereafter scanned in a micro CT-scanner (Nanotome from General Electric Inspection Technologies) along with hydroxyapatite phantom standards. Cylindrically shaped samples prepared ex vivo and allowed to set and harden in saline water for 24 h at 37° C. were also scanned in order to obtain data from the zero time point. After scanning, bone samples were sawed into 4 mm thick slices and returned into the buffered fixative for minimum of additional 4 weeks. After completing the fixation period, samples were put into 15% EDTA solution at neutral pH for decalcification for up to 4 months with regular renewal of the EDTA solution. After decalcification, samples were prepared for histology (paraffin) and stained using hematoxylin-eosin.

Micro CT Analysis

Primary micro CT data was subjected to volume reconstruction and data analysis using Datos-X software and Volume Graphics studio Max 2.0 from Volume Graphics. The reconstructed volume comprised the entire hypophysis of the tibia, reaching from the tibial plateau and 3 cm downwards comprising the drillhole and all possible implant material which might be found outside the drillhole. Through gray value cut off/gray value definition, the volume of old bone, new bone and implant material within this reconstructed volume was determined. Higher concentrations of hydroxyapatite in the standards appear in the micro CT images with a brighter grayscale value ("more white"). As hydroxyapatite is the main constituent in calcified bone inducing x-ray attenuation, the grayscale values of the standards can be used to estimate the degree and distribution of mineralization in the samples. By comparing the grayscale values of the hydroxyapatite standards and of the samples, the degree of mineralization could thus be judged. The brightest areas in the CT images indicate tissue with the highest degree of mineralization.

Figure 7:
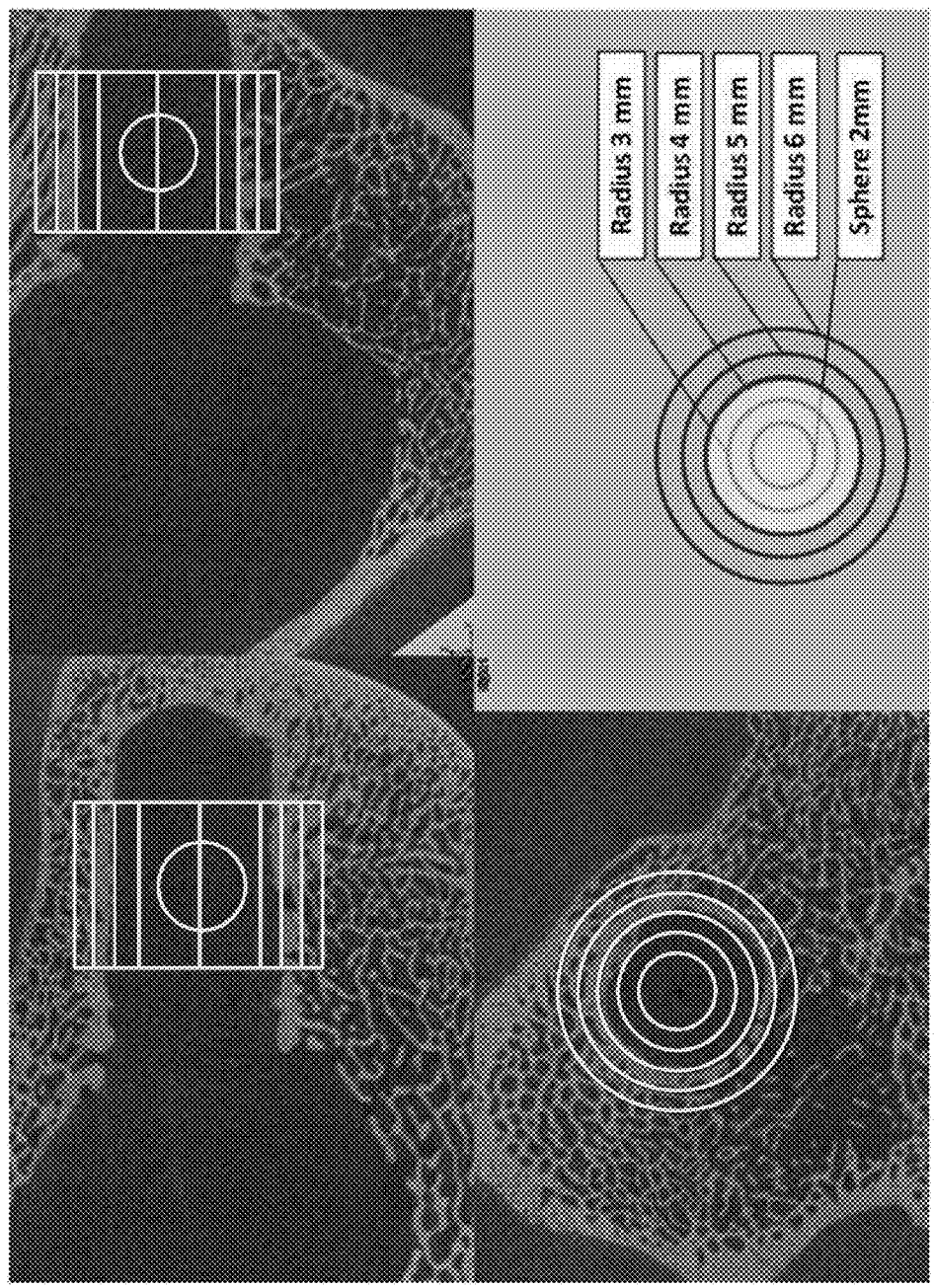
FIG. 7: Micro CT construct of empty hole in sheep tibia left leg of an animal receiving composition of the current invention in the right leg tibia. The figure represents transverse sections in three different planes (x, y and z) after 3 months post operation (see Example 4). The figure shows how virtual cylinders with different radiuses were created, concentric to the drill hole.

For quantitative evaluation, a virtual cylinder of 4 mm in length and radius of 3 mm was defined and carefully and concentrically orientated with the longitudinal axis in the direction of the drill hole (FIG. 7). While keeping the orientation of the cylinder fixed, the radius was increased stepwise to 4, 5 and 6 mm and the mineral volume in each cylinder measured. This analysis was repeated in all samples, both empty holes (left tibia) and holes with implant. By subtracting narrower cylinder from broader, such as radius 3 mm from radius 4 mm (R4-R3), R5-R4 and R6-R5, mineral phase volume of a 1 mm outer shell (tube) of each cylinder was obtained. Mineral phase volume of the shell of all cylinders was normalized to a standard volume of 1 $mm^3$ obtaining mineral density and this data was analyzed statistically using the SigmaStat and SigmaPlot software.

Results

Cross section micro CT images were prepared from all samples showing the implanted material and surrounding tissues in 3 planes. These images were used for visual evaluation and to define the virtual cylinders used for quantitative evaluation of mineral density.

Histological sections were used for evaluation of tissue responses to the implanted material with emphasis on signs of inflammation, foreign body reaction, scar tissue formation and newly formed bone tissue.

Interpretation of Micro CT Data

Figure 8:
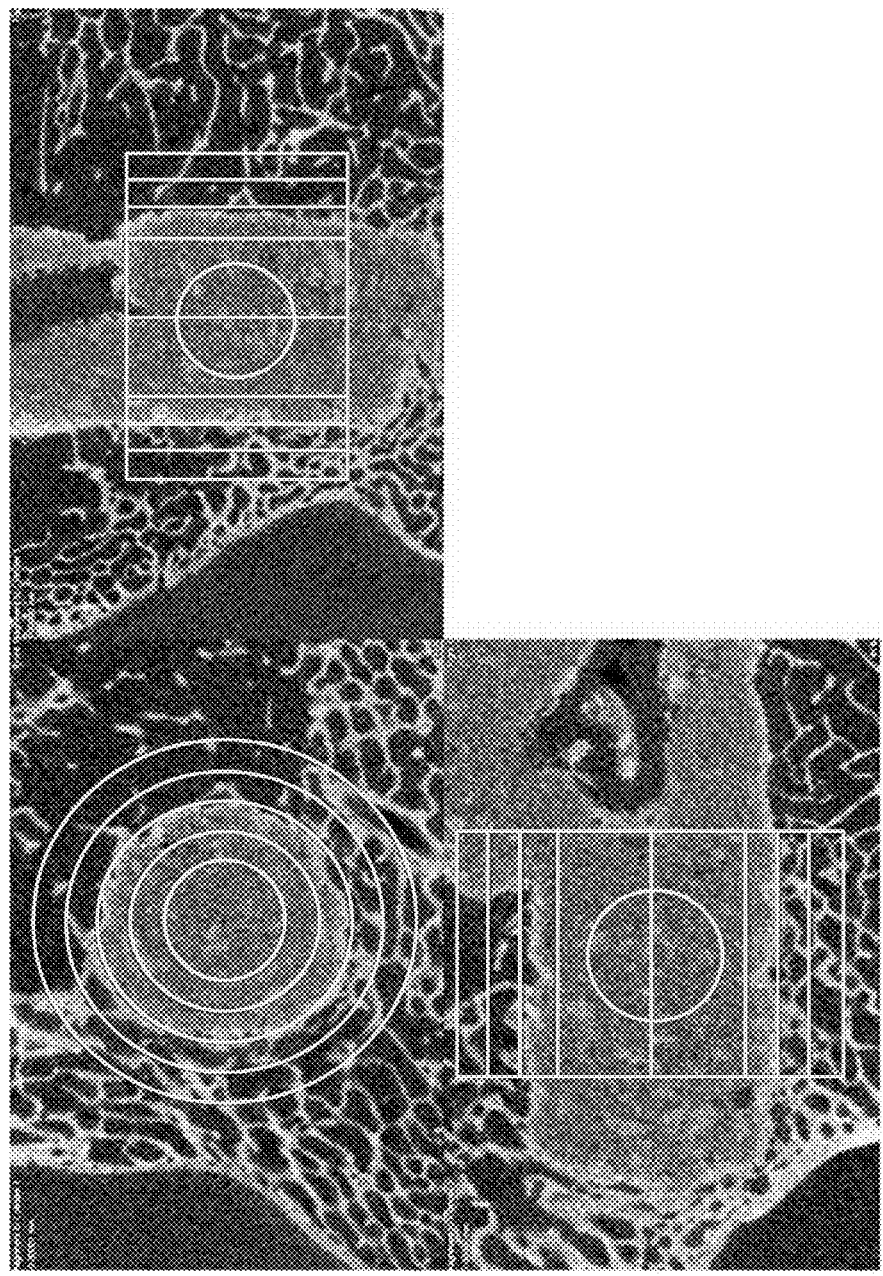
FIG. 8: Micro CT constructs of right leg tibia receiving composition of the current invention in three different planes (x, y and z) 3 months post operatively in vivo. Dense mineralized tissue can be noticed along the surface of the composition along with scattered islands of mineralized tissue throughout the interior of the implanted composition.

After 3 months in vivo, visual evaluation revealed a dense shell of apparent new bone surrounding the implant and well connected to the adjacent trabecular bone tissue. Islands of dense structures inside the implant indicated bone formation scattered throughout the material (FIG. 8). After 13 months in vivo this was even more pronounced, the surrounding shell appeared to be thicker and bone formation within the implant was much more pronounced than after 3 months in vivo.

Figure 9:
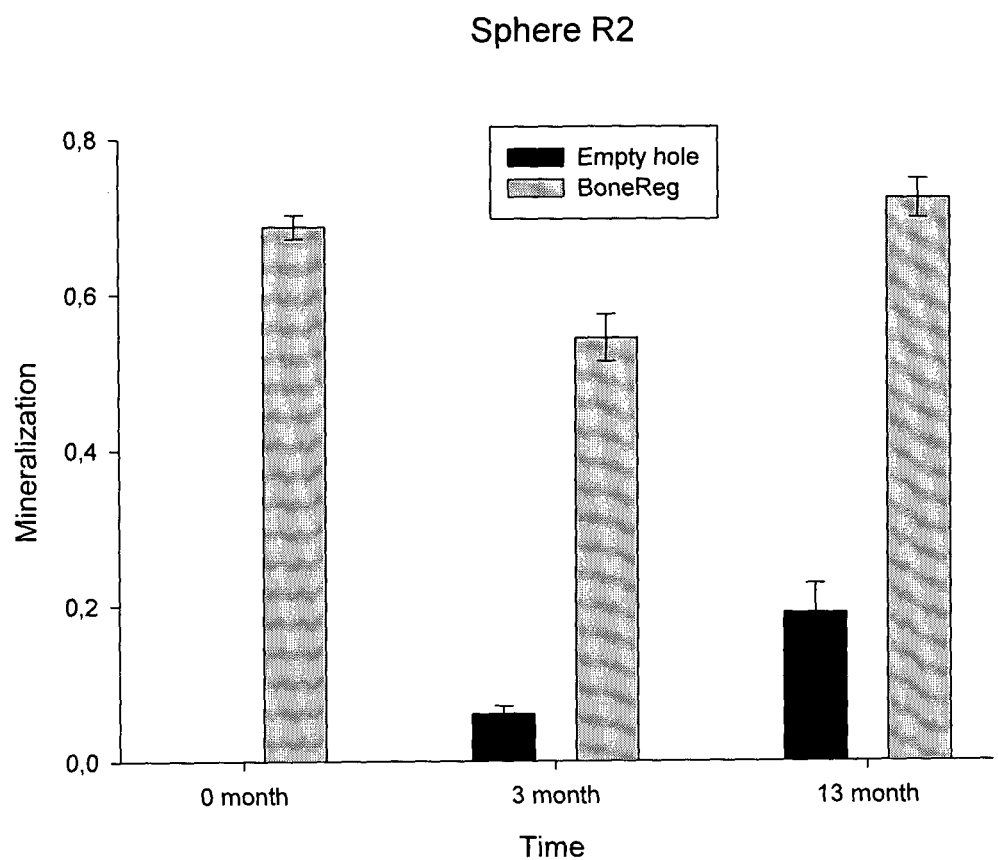
FIG. 9: Mineralization (per $mm^3$) inside a virtual sphere created with a radius of 2 mm inside an implanted composition of this invention. (See Example 4.)

Statistical evaluation of mineral density in ex vivo samples and in vivo samples revealed 21% reduction of mineral density during 3 months in vivo. Between 3 and 13 months in vivo, mineral density of the implant had increased again by 33% (FIG. 9).

Figure 10:
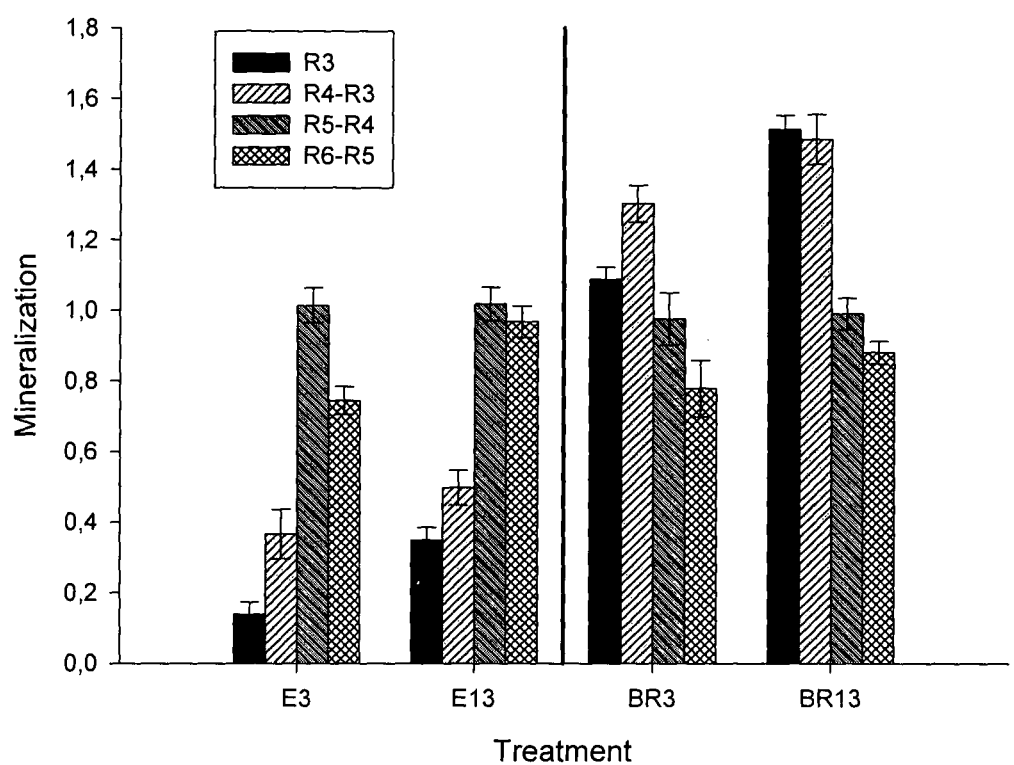
FIG. 10: Bone mineralization (per $mm^3$) in the virtual cylinder R3 and in the virtual shells R4-R3, R5-R4 and R6-R5. (See Example 4.) Empty hole is denoted by E and hole filled with a composition of current invention is denoted by BR.

At 3 months and 13 months the empty holes did not appear to have any in growth of mineralized tissue. However, a thin shell of dense bone tissue was apparent surrounding the empty hole. This was confirmed by quantitative assessment of the R4-R3 data (FIG. 10). This revealed that the 8 mm drill hole was a critical bone gap in this model.

Implant and bone changes were quantified by measuring gray value distribution at 3 months and 13 months, using MATLAB (MATrix LABoratory) and MIMICS (medical imaging segmentation software) software. The results demonstrate a distinctive difference in gray value distribution between the implant and bone at 3 months. However, at 13 months, gray value distribution of the implant had changed to become similar to the gray value distribution of the surrounding bone. These results suggest morphological change of the implant during the 10 months period indicating a progressive conversion of implant material to bone tissue.

Confirmation by Histological Analysis

Figure 11:
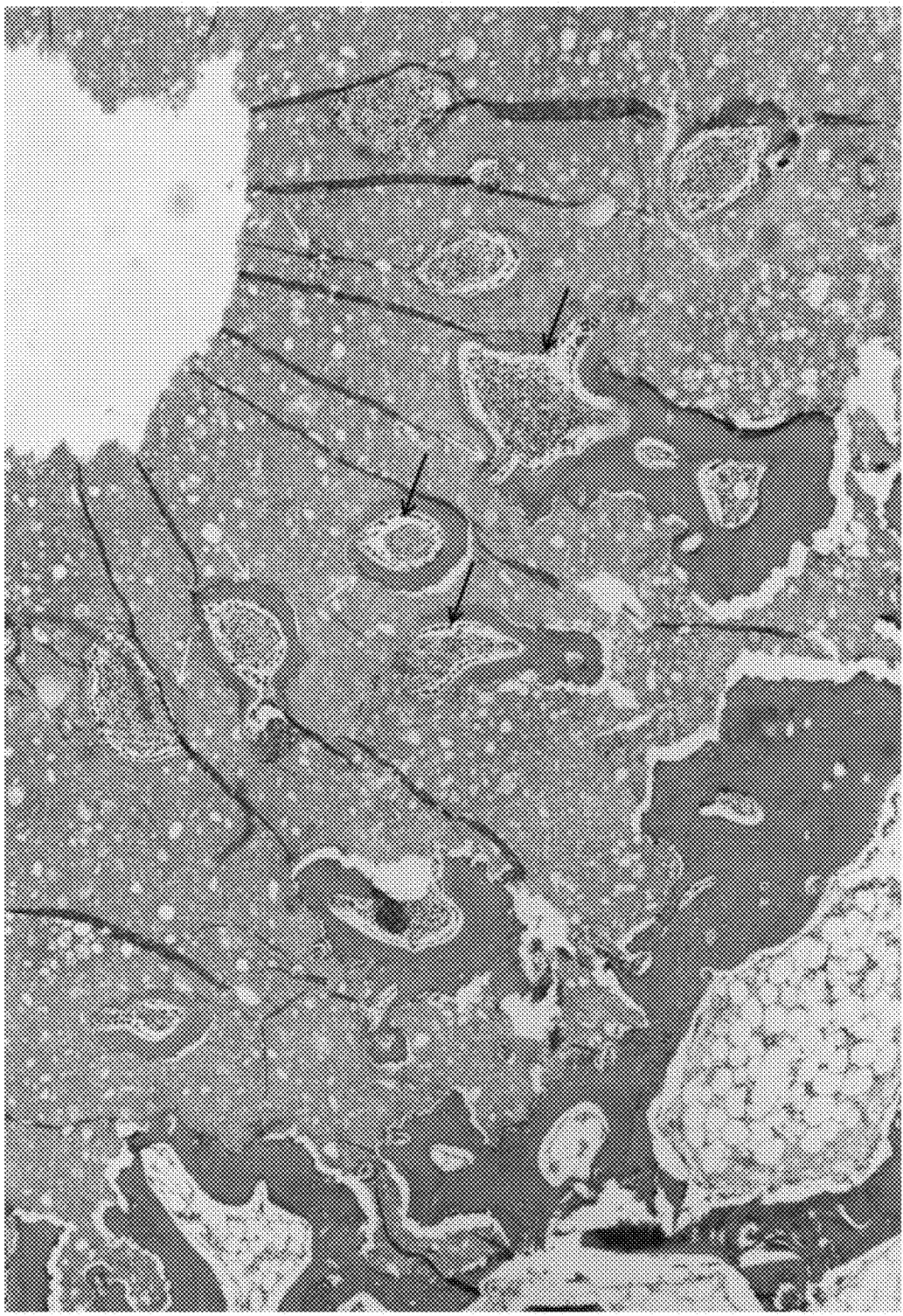
FIG. 11: Microscopic image of implanted composition of the current invention showing formations of new bone inside the implanted composition (see Example 4).

Histological evaluation of tibia after 3 months showed that the implant material was fully biocompatible with no sign of inflammation or foreign body reaction. Scar tissue formation was negligible. A shell of new bone tissue with intense integration to the adjacent trabecular bone was apparent surrounding the entire implant, and islands of new bone were scattered throughout the implant (FIG. 11). Lining images of histological sections with homolog images of micro CT sections confirmed that areas characterized by high density (highest degree of X-ray attenuation) surrounding and scattered throughout the implant, was newly formed bone tissue.

The invention claimed is:

1. A composition kit for bone healing medical treatment, comprising
    a. a solid fraction, comprising partially deacetylated chitin (PDC) with a degree of deacetylation in the range of 40-75%, and calcium phosphate;
    b. an acidic liquid fraction comprising water and an acid;
    said fractions being provided in separate vials, to be mixed prior to use, wherein the weight:weight ratio of the solids to liquid fraction is in the range from 1:1.2 to 1:6.

2. The composition kit of claim 1, wherein the PDC has a degree of deacetylation in the range of 40-60%.

3. The composition kit of claim 1, wherein said solids fraction comprises in the range of 3-30 wt %.

4. The composition kit of claim 1, wherein said liquid fraction comprises one or more acid selected from the group consisting of phosphoric acid, hydrochloric acid, ascorbic acid, lactic acid, acetic acid, formic acid, propionic acid, malic acid, citric acid and glutamic acid.

5. The composition kit of claim 1, wherein said liquid fraction has an acidity equivalent to at least 5 wt % phosphoric acid.

6. The composition kit of claim 1, wherein said liquid fraction further comprises calcium hydroxide.

7. The composition kit of claim 1, wherein the weight ratio of said solids to liquid fraction is in the range of about 1:1.3 to about 1:4.

8. The composition kit of claim 7, wherein the weight ratio of said solids to liquid fraction is in the range of about 1:1.5 to about 1:3.

9. The composition kit of claim 1, comprising an amount of PDC which is in the range of 0.5-10% wt of the combined fractions.

10. The composition kit of claim 1, wherein said PDC has been dissolved and precipitated.

11. The composition kit of claim 1, wherein said calcium phosphate comprises one or more of tetracalcium phosphate, alfa-tricalcium phosphate, and other calcium phosphates that can form precipitates of hydroxyapataite and/or brushite.

12. The composition kit of claim 1, wherein said solids fraction comprises sodium glycerol phosphate.

13. The composition kit of claim 1, wherein the composition starts to harden at room temperature after mixing, and has a setting time at room temperature within the range of about 15-30 minutes.

14. The composition kit of claim 13, said composition having a viscosity after mixing as determined by injectability, which is less than 30 N when measured with 5 mL B.Braun syringe with 12 mm ID and 2 mm outlet.

15. The composition kit of claim 1, wherein said composition does not include bone morphogenic protein or other biological factor selected from bone marrow, blood, bone, and osteogenic proteins.

16. The composition kit of claim 1, further comprising calcium sulphate in the solids fraction.

17. The composition kit of claim 1, which is sterilized with gamma irradiation.

18. The composition kit of claim 1, wherein the PDC has a degree of deacetylation which is about 50%.

19. The composition kit of claim 1, wherein said solids fraction comprises in the range of 5-15 wt % PDC.

20. The composition kit of claim 1, comprising an amount of PDC which is in the range of 1-5% wt of the combined fractions.

21. A method of bone healing, comprising:
    mixing together a solid fraction, comprising partially deacetylated chitin (PDC) with a degree of deacetylation in the range of 40-75%, and calcium phosphate, and an acidic liquid fraction comprising water and an acid, wherein the weight:weight ratio of the solid fraction to liquid fraction is in the range from 1:1.2 to 1:6, to form a mix which is a liquid, semi-liquid or paste-like cement mix;
    applying the obtained mix to the site of bone to be healed.

22. The method of claim 21, wherein said applying is by injection.

23. The method of claim 21, wherein said applying is by applying to bone surface using an instrument.

24. The method of claim 21, wherein the weight:weight ratio of the solid fraction to liquid fraction is in the range about 1:1.3 to about 1:4.

* * * * *